US00RE34997E

United States Patent [19]

Kraenzle

[11] E Patent Number: Re. 34,997

[45] Reissued Date of Patent: Jul. 18, 1995

[54] DENTAL APPLIANCE

[76] Inventor: David Kraenzle, 511 Sarah La., St. Louis, Mo. 63141

[21] Appl. No.: 146,732

[22] Filed: Oct. 29, 1993

Related U.S. Patent Documents

Reissue of:

[64] Patent No.: 5,224,859
Issued: Jul. 6, 1993
Appl. No.: 920,805
Filed: Jul. 28, 1992

[51] Int. Cl.[6] ..... A61C 1/08; A61C 1/14

[52] U.S. Cl. ..... 433/126; 433/127

[58] Field of Search ..... 433/114, 116, 125, 126, 433/127

[56] References Cited

U.S. PATENT DOCUMENTS

| | | | |
|---|---|---|---|
| 186,471 | 1/1877 | Gilbert . | |
| 186,504 | 1/1877 | Starr . | |
| 307,686 | 11/1884 | Starr . | |
| 1,522,757 | 1/1925 | Thiedemann . | |
| 1,534,817 | 4/1925 | Thiedeman et al. . | |
| 1,838,982 | 12/1931 | Angell . | |
| 1,982,336 | 11/1934 | Wiseman | 32/27 |
| 2,010,421 | 8/1935 | Terry | 32/27 |
| 2,090,885 | 8/1937 | Clark | 32/27 |
| 2,738,528 | 3/1956 | Fridge, Sr. | 32/27 |
| 2,766,470 | 10/1956 | Baker | 15/28 |
| 3,163,934 | 1/1965 | Wiseman | 32/27 |
| 3,389,468 | 6/1968 | Lewis et al. | 32/59 |
| 3,407,502 | 10/1968 | Richmond | 32/59 |
| 3,672,060 | 6/1972 | Eibofner et al. . | |
| 3,727,313 | 4/1973 | Graham | 32/27 |
| 3,798,777 | 3/1974 | Reiter | 32/27 |
| 4,014,099 | 3/1977 | Bailey | 32/27 |
| 4,021,918 | 5/1977 | Bailey | 32/27 |
| 4,040,311 | 9/1977 | Page, Jr. et al. | 74/750 |
| 4,053,983 | 10/1977 | Flatland | 32/27 |
| 4,182,041 | 1/1980 | Girard | 433/115 |
| 4,234,308 | 11/1980 | Leonard | 433/127 |
| 4,253,832 | 3/1981 | Bailey | 433/115 |
| 4,266,933 | 5/1981 | Warden et al. | 433/82 |
| 4,285,671 | 8/1981 | Lustig et al. | 433/126 |
| 4,292,027 | 9/1981 | Richmond | 433/127 |
| 4,310,310 | 1/1982 | Bailey | 433/126 |
| 4,365,956 | 12/1982 | Bailey | 433/115 |
| 4,406,621 | 9/1983 | Bailey | 433/126 |
| 4,449,932 | 5/1984 | Lustig | 433/126 |
| 4,533,324 | 8/1985 | Nakanishi | 433/132 |
| 4,544,356 | 10/1985 | Gardella et al. | 433/122 |
| 4,564,354 | 1/1986 | Rosenstatter | 433/133 |
| 4,575,338 | 3/1986 | Maizenberg | 433/126 |
| 4,604,058 | 8/1986 | Fisher et al. | 433/127 |
| 4,911,639 | 3/1990 | Jacklich | 433/102 |
| 5,020,994 | 6/1991 | Huang | 433/126 |
| 5,028,233 | 7/1991 | Witherby | 433/125 |
| 5,040,978 | 8/1991 | Falcon et al. | 433/125 |
| 5,040,979 | 8/1991 | Kuhn | 433/126 |
| 5,040,980 | 8/1991 | Heil | 433/127 |
| 5,090,904 | 2/1992 | Bailey | 433/88 |
| 5,094,615 | 3/1992 | Bailey | 433/88 |
| 5,156,547 | 10/1992 | Bailey | 433/125 |

FOREIGN PATENT DOCUMENTS 328171 10/1920 Germany .

OTHER PUBLICATIONS

Young Dental Company product (embodiment of disclosure of U.S. Pat. No. 5,156,547).
Three photos of dental appliances.
Star Dental Price List.
Intra Lux Price List.

*Primary Examiner*—Nicholas D. Lucchesi
*Attorney, Agent, or Firm*—Senniger, Powers, Leavitt & Roedel

[57] ABSTRACT

A dental appliance having an elongated hollow body including a tubular handle and a tubular extension. The extension has at its forward end a recessed forward end formation defining a forwardly opening recess. A closure mates with the forward end formation on the recess on a mating plane generally transverse to the axis of the bore in the extension. The recessed forward end formation of the extension and the closure define a chamber at the forward end of the extension when the closure is applied. The bore in the extension is accessible from the forward end of the extension when the closure is away from the forward end of the extension for assembly of the appliance.

14 Claims, 1 Drawing Sheet

DENTAL APPLIANCE

Matter enclosed in heavy brackets [ ] appears in the original patent but forms no part of this reissue specification; matter printed in italics indicates the additions made by reissue.

BACKGROUND OF THE INVENTION

This invention relates to a dental appliance and more specifically, to a dental prophylaxis angle which opens forwardly to provide access to the appliance interior, thereby facilitating assembly. The invention is also directed to a method for assembling a dental appliance.

Dental appliances of this nature typically include a hollow head on the end of an elongated, hollow body. A drive shaft within the body drives a rotor in the head of the appliance. At the rearward end of the appliance, i.e., the end remote to the head, the drive shaft is driven by a drive mechanism. These appliances are often cumbersome to assemble and include components which are difficult to manufacture. Additionally, these appliances are commonly constructed of lightweight, inexpensive plastic so that they are disposable and may be discarded after use, thus obviating the expense and inconvenience of sterilization. Inexpensive plastic materials, however, do not lend themselves to use in connection with a dental appliance which is sturdy and easily assembled and which operates smoothly and consistently.

SUMMARY OF THE INVENTION

It is an object of this invention, therefore, to provide an improved dental appliance, more particularly, to provide an improved prophylaxis angle which is easily assembled, of sturdy construction and which operates smoothly and consistently. It is a further object to provide such an appliance which is disposable and constructed of plastic materials, the components of which may be manufactured easily and inexpensively. It is a still further object to provide a method for assembling a dental appliance.

Briefly, therefore, the invention is directed to a dental appliance which has an elongated hollow body comprising a tubular handle and a tubular extension extending from the handle at one end thereof. The extension has a bore therethrough from the end thereof at the handle to its other end constituting its forward end. The extension has at its forward end a recessed forward end formation defining a forwardly opening recess. The appliance also has a closure for the forwardly opening recess mating with the forward end formation on the recess. The recessed forward end formation of the extension and the closure define a chamber at the forward end of the extension when the closure is applied to the recessed forward end formation. The closure mates with the forward end formation on a plane generally transverse to the axis of the bore in the extension. The appliance has a rotor rotatable in the chamber on an axis transverse to the axis of the bore. A drive shaft extending through the bore has a forward end in said chamber. A gear on the forward end of the drive shaft mates with a gear on the rotor.

The invention is further directed to a dental appliance which has an elongated hollow body comprising a tubular handle and a tubular extension extending from the handle at one end thereof. The extension has a bore therethrough from the end thereof at the handle to its other end constituting its forward end. The extension has at its forward end a recessed forward end formation defining a forwardly opening recess. The appliance also has a closure for the forwardly opening recess mating with the forward end formation on the recess. The recessed forward end formation of the extension and the closure define a chamber at the forward end of the extension when the closure is applied to the recessed forward end formation. The closure mates with the forward end formation on a plane generally transverse to the axis of the bore in the extension. The appliance has a rotor rotatable in the chamber on an axis transverse to the axis of the bore. A drive shaft extending through the bore has a forward end in said chamber. A gear on the forward end of the drive shaft mates with a gear on the rotor. The gear on the forward end of the drive shaft is of larger diameter than the drive shaft and the bore and engages the forward end of the extension to hold the drive shaft against rearward movement in the bore. The bore in the extension is accessible from the forward end of the extension when the closure and the rotor are away from the forward end of the extension for assembly of the appliance by insertion of the drive shaft with its gear thereon in the bore from the forward end of the extension. The rotor is placed in the recess and the gear on the rotor mates with the gear on the drive shaft. The closure is secured to the forward end formation to house the rotor in said chamber.

Other objects and features of the invention will be in part apparent and in part pointed out hereinafter.

DETAILED DESCRIPTION OF THE PREFERRED EMBODIMENTS

Figure 1:
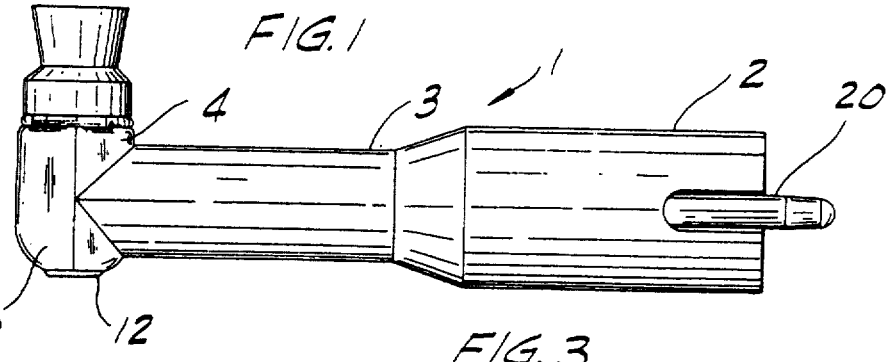
FIG. 1 is a side elevation of the assembled dental appliance of the invention.
Figure 2:
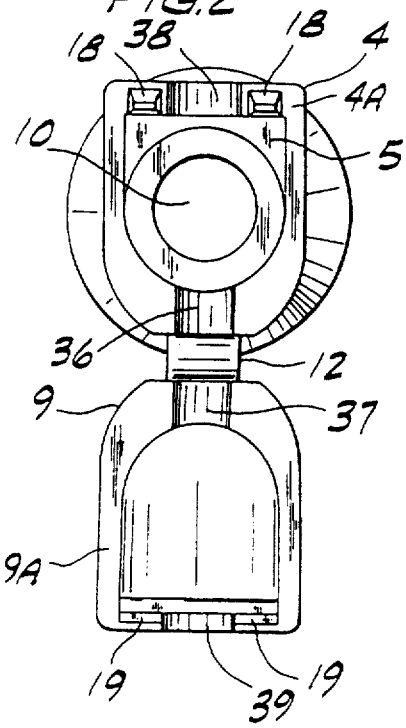
FIG. 2 is an end view from the forward end of the dental appliance, open for assembly.

Referring to FIG. 1, there is indicated at 1 an elongated hollow body of the dental appliance of the invention. The appliance includes tubular handle 2 and tubular extension 3 extending forwardly from handle 2. Formation 4 is positioned at the forward end of tubular extension 3 and as shown in FIG. 2, is a recessed end formation which forwardly opens and defines a forwardly opening recess indicated generally at 5. *As shown in FIG. 2, formation 4 has a rim 4A at its forward end.* Because this *recessed end formation opens forwardly, access is provided* to the interior of the tubular extension. As will be seen hereinbelow, such access advantageously facilitates assembly of the appliance.

Figure 3:
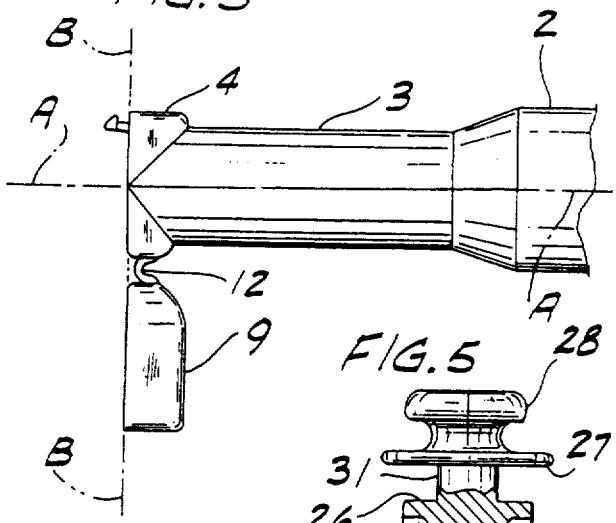
FIG. 3 is a partial side elevation of the dental appliance, open for assembly.
Figure 4:
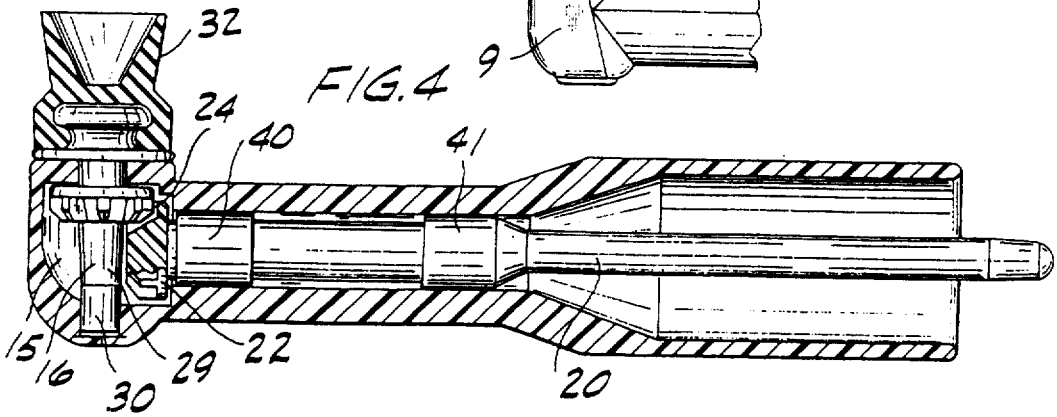
FIG. 4 is longitudinal section of the assembled dental appliance.

At 9 is indicated a closure, shown in its secured, closed position applied to end formation 4 in FIGS. 1 and 4 and in its open, unapplied, unsecured position away from formation 4 in FIGS. 2 and 3. *As shown in FIG. 2, closure 9 has a rim 9A.* When closure 9 is in its unapplied position, access to bore 10 of the tubular extension is provided. Closure 9 is movable between secured and unsecured positions and, at the user's option, may be a separate piece from, or integral with formation 4. In the preferred embodiment, closure 9 is integral with formation 4 and attached thereto by means of hinge 12. In this embodiment, body 1, which includes formation 4, hinge 12 and closure 9 are integral, preferably co-molded as a single plastic construction of a material such as Lexan available from General Electric Co. Co-molding of the closure, hinge and body as a single piece facilitates assembly of a sturdy, smoothly operating appliance.

Figure 6:
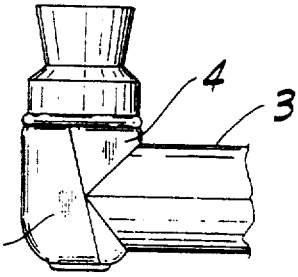
FIG. 6 is a side elevation of an alternative embodiment of the dental appliance of the invention.

The longitudinal axis of the bore is indicated at A in FIG. 3. *The rim 9A of* Closure 9 mates with *the rim 4A of* formation 4 along the plane including axis B, which is transverse to axis A, the longitudinal axis of the bore extending through body 1 and extension 3. In this embodiment the mating plane is perpendicular to axis A, but other embodiments of the invention provide for mating of the closure with the forward end formation on a plane which is generally transverse, but perhaps not perpendicular, to axis A. These other embodiments are included among those embodiments in which the mating plane is angled to a degree about one or more of a number axes intersecting the transverse plane, such as axis B and/or the axis perpendicular to axis A and perpendicular to axis B. The degree to which the mating plane may be angled must not be such, however, that access to bore 10 of the tubular extension is significantly restricted when closure 9 is away from formation 4. For example, if it is decided to angle the mating plane about axis B from its position illustrated in FIG. 3, it should be angled less than 90°, preferably less than about 60°, more preferably less than about 45°, (see FIG. 6) and most preferably less than about 30°.

FIG. 4 illustrates that when closure 9 is in its closed, secured position, applied to formation 4, closure 9 and the forwardly opening recess 5 (FIG. 2) defined by recessed end formation 4 cooperate to define chamber 15 at the forward end of tubular extension 3. Latch means, specifically, latch elements 18 and recesses 19 on the periphery of the forwardly opening end formation and closure, respectively, matingly cooperate to securely latch closure 9 to forwardly opening recessed end formation 4 by snap interengagement upon application of closure 9 thereto. Although the illustrated embodiment has two elements and mating recesses, other embodiments of the invention include one such element or three or more such elements. Still other embodiments of the invention provide for securement of the closure to the end formation by means other than latch means, including adhesive and other fastening means. It is also contemplated that the closure may be a separate piece from the forward end formation. In such embodiments, it may be desirable to space a plurality of latch elements around the periphery of the closure. The securement means selected may provide for permanent securement of the closure to the end formation or may provide for releasable securement, depending on whether it is desirable to be able to access to the chamber and bore subsequent to initial assembly. Certain types of securement means which provide for permanent attachment may result in a sturdier and smoother operating appliance than their releasable counterparts.

Drive shaft 20 is positioned within body 1 along bore axis A and includes gear 22 on the forward end thereof. As shown in FIG. 4, when the appliance is in assembled condition, the forward end of drive shaft 20 extends into chamber 15. In this particularly preferred embodiment, gear 22 is of larger diameter than the drive shaft and the bore and engages the forward end of tubular extension 3 to hold the drive shaft against rearward movement in the bore. Drive shaft 20 also includes bearings 40 and 41 for facilitating smooth rotation of the drive shaft within the bore. Chamber 15 houses rotor 16 such that gear 22 on the drive shaft mates with gear 24 on the rotor. Gears 22 and 24 are shown here as Gleason type gears but may be other bevel or other type gears. Drive shaft 20 is driven at its rearward end and thereby drives rotor 16 which is rotatable in the chamber. Rotor 16 and drive shaft 20 are preferably molded from a plastic material such as Celcon available from Celanese Corp.

Figure 5:
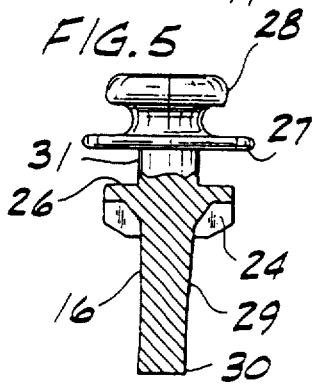
FIG. 5 is a side elevation of the rotor of the dental appliance, partly in section.

In FIG. 5 is shown rotor 16 in its preferred embodiment, having shoulder 26, shaft 27, button 28, shank 29, extension 30, and upper shank 31. The rotor may also be a burr or include another dental tool to be rotatably driven such as a brush. Button 28 is shaped to receive and retain rubber prophylaxis cup 32 by snap engagement. Rotor 16 may also be configured to receive a prophylaxis cup by screw type attachment or otherwise. Shelf 27 bears on closure 9 and end formation 4 and supports cup 32 as shown in FIGS. 1 and 4. Shelf 27 prevents downward movement, and shoulder 26 prevents upward movement, of the rotor relative to the chamber. Shank 29 is slightly tapered so that its upper portion accepts any forward load which may be applied via drive shaft 20. The upper portion of shank 29, unlike its lower portion, advantageously travels in the same direction as that area of gear 22 which it contacts. Extension 30 extends into a recess cooperatively formed by semicircular recesses 36 and 37 upon application of closure 9 to end formation 4. Smooth, sturdy rotational operation of the rotor is facilitated by the positioning of extension 30 in this cooperatively formed recess.

In assembling this dental appliance, body 1 is provided in its condition where closure 9 is away from formation 4. In the embodiment shown in FIGS. 2 and 3, for example, the closure is hingedly opened providing access to the bore and to the forwardly opening recess defined by formation 4. With formation 4 opening forwardly, drive shaft 20 is readily inserted into bore 10 at the forward end of the body. Drive shaft 20 is inserted to a depth whereby gear 22 engages the forward end of extension 3. Rotor 16 is placed in the forwardly opening recess such that its gears 24 mate with the gears 22 of the drive shaft. Extension 30 of the rotor is placed against semicircular recess 36 and upper shank 31 is placed against semicircular recess 38. Closure 9 is applied to recessed and formation 4, thus defining a chamber which houses the rotor. *The rotor axis is generally coincident with the plane on which the rim face 9A of the closure mates in abutting relationship with the rim face 4A of the end formation.* Semicircular recess 36 mates with semicircular recess 37, and semicircular recess 38 mates *in directly opposed relationship* with semicircular recess 39 to form cylindric openings constituting bears for the rotor. The closure, rotor and drive shaft are secured in place by securement of the closure to the end formation of the extension. Rubber prophylaxis cup 32 is then snapped onto button 28.

In view of the above, it will be seen that the several objects of the invention are achieved.

Although specific examples of the present invention and its application are set forth herein, it is not extended that they are exhaustive or limiting of the invention. These illustrations and explanations are intended to acquaint other skilled in the art with the invention, its principles, and its practical application, so that others skilled in the art may adapt and apply the invention in its numerous forms, as may be best suited to the requirements of a particular use.

What is claimed is:

1. A dental appliance comprising:

an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a forwardly opening recess;

a closure for said recess mating with said recessed forward and formation on said recess;

said recessed forward end formation of the extension and said closure defining a chamber at said forward end of the extension when said closure is applied to said recessed forward end formation;

a rotor rotatable in the chamber on an axis transverse to the axis of the bore;

a drive shaft extending through said bore having a forward end in said chamber;

a gear on the forward end of the drive shaft mating with a gear on the rotor;

*said end formation and closure being formed with cooperable semicircular bearing recesses which mate in directly opposed relationship on opposite sides of a plane generally transverse with respect to the axis of said bore in the extension to provide generally cylindric bearing means for the rotor when the closure mates with said end formation.*

2. The dental appliance of claim 1 wherein said closure mates with said forward end formation on a plane generally transverse to the axis of said bore in the extension.

3. [The dental appliance of claim 2] *A dental appliance comprising:*

*an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a forwardly opening recess;*

*a closure for said recess mating with said recessed forward end formation on said recess on a plane generally transverse to the axis of said bore in the extension;*

*said recessed forward end formation of the extension and said closure defining a chamber at said forward end of the extension when said closure is applied to said recessed forward end formation;*

*a rotor rotatable in the chamber on an axis transverse to the axis of the bore;*

*a drive shaft extending through said bore having a forward end in said chamber;*

*a gear on the forward end of the drive shaft mating with a gear on the rotor* wherein the gear on the forward end of the drive shaft is of larger diameter than the drive shaft and the bore and engages the forward end of the extension to hold the drive shaft against rearward movement in the bore;

the bore in said extension being accessible from the forward end of the extension when the closure and the rotor are away from the forward end of the extension for assembly of the appliance by insertion of the drive shaft with its gear thereon in the bore from the forward end of the extension, followed by placement of the rotor in said recess and mating of the gear on the rotor with the gear on the drive shaft, and then followed by securement of the closure to the forward end formation to house the rotor in said chamber;

*said end formation and closure being formed with cooperable semicircular bearing recesses which mate on opposite sides of a plane generally transverse with respect to the axis of said bore in the extension to provide generally cylindric bearing means for the rotor when the closure mates with said end formation.*

[4. The dental appliance of claim 2 wherein the elongated hollow body is molded of plastic in one piece.]

[5. The dental appliance of claim 2 further comprising] *A dental appliance comprising:*

*an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a forwardly opening recess;*

*a closure for said recess mating with said recessed forward end formation on said recess on a plane generally transverse to the axis of said bore in the extension;*

*said recessed forward end formation of the extension and said closure defining a chamber at said forward end of the extension when said closure is applied to said recessed forward end formation;*

*a rotor rotatable in the chamber on an axis transverse to the axis of the bore;*

*a drive shaft extending through said bore having a forward end in said chamber;*

*a gear on the forward end of the drive shaft mating with a gear on the rotor; and* a hinge whereby the closure is hinged to the end formation;

*said end formation and closure being formed with cooperable bearing recesses which mate to provide generally cylindric bearing means for the rotor when the closure mates with said end formation.*

6. The dental appliance of claim 5 wherein the body, closure and hinge are molded of plastic in one piece.

7. The dental appliance of claim 6 wherein the rotor extends through an opening at one side of the chamber and the hinge is at another side of the chamber.

[8. The dental appliance of claim 2 wherein the end formation and closure are formed with semicircular recesses which mate when the closure is in place to provide cylindric openings constituting bearings for the rotor. ]

9. *A dental appliance comprising:*

*an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a forwardly opening recess;*

*a closure for said recessed mating with said recessed forward end formation on said recess on a plane generally transverse to the axis of said bore in the extension;*

*said recessed forward end formation of the extension and said closure defining a chamber at said forward end of the extension when said closure is applied to said recessed forward end formation;*

*a rotor rotatable in the chamber on an axis transverse to the axis of the bore;*

*a drive shaft extending through said bore having a forward end in said chamber;*

*a gear on the forward end of the drive shaft mating with a gear on the rotor wherein the gear on the forward end of the drive shaft is of larger diameter than the drive shaft and the bore and engages the forward end of the extension to hold the drive shaft against rearward movement in the bore;*

*the bore in said extension being accessible from the forward end of the extension when the closure and the rotor are away from the forward end of the extension for assembly of the appliance by insertion of the drive shaft with its gear thereon in the bore from the forward end of the extension, followed by placement of the rotor in said recess and mating of the gear on the rotor with the gear on the drive shaft, and then followed by securement of the closure to the forward end formation to house the rotor in said chamber;*

*said end formation and closure being formed with cooperable bearing recesses which mate to provide generally cylindric bearing means for the rotor when the closure mates with said end formation; and*

[The dental appliance of claim 2 further comprising] at least one latch means for latching the closure to the end formation.

10. The dental appliance of claim 9 wherein said closure is latched to said end formation by snap interengagement.

11. The dental appliance of claim [2] *3* wherein the rotor comprises a button for retention of a prophylaxis cup thereon.

12. A dental appliance comprising:

an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a substantially forwardly opening recess, *said end formation having a forwardly facing rim face at its forward end lying in a plane generally transverse with respect to the axis of said bore in the extension ;* a closure for said recess *having a rearwardly facing rim face* mating *in abutting relationship* with *the forwardly facing rim face of* said forward end formation on *said generally transverse plane when the closure is applied to said recessed forward end formation,* [a plane which is angled less than 45° from the plane which is perpendicular to the axis of said bore in the extension];

said recessed forward end formation of the extension and said closure defining a chamber at said forward end of the extension when said closure is applied to said recessed forward end formation;

a rotor rotatable in the chamber on an axis transverse to the axis of the bore, *said rotor axis being generally coincident with the plane on which the rearwardly facing rim face of the closure and the forwardly facing rim face of the extension mate in abutting relationship;* a drive shaft extending through said bore having a forward end in said chamber; *and* a gear on the forward end of the drive shaft mating with a gear on the rotor.

[13. The dental appliance of claim 12 wherein said closure mates with said forward and formation on a plane which is angled less than 30° from the plane which is perpendicular to the axis of said bore in the extension.]

14. A dental appliance comprising:

an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a forwardly opening recess;

a closure for said recess mating with said forward end formation on said recess on a plane generally transverse to the axis of said bore in the extension;

a hinge whereby the closure is hinged to the forward end formation;

said recessed forward end formation of the extension and said closure defining a chamber at said forward end of the extension when said closure is applied to said recessed forward end formation;

a rotor rotatable in the chamber on an axis transverse to the axis of the bore;

a drive shaft extending through said bore having a forward end in said chamber;

a gear on the forward end of the drive shaft mating with a gear on the rotor, the gear on the forward end of the drive shaft being of larger diameter than the drive shaft and the bore for engagement of the forward end of the extension to hold the drive shaft against rearward movement in the bore;

the bore in said extension being accessible from the forward end of the extension when the closure and the rotor are away from the forward end of the extension for assembly of the appliance by insertion of the drive shaft with its gear thereon in the bore from the forward end of the extension, followed by placement of the rotor in said recess and mating of the gear on the rotor with the gear on the drive shaft, and then followed by securement of the closure to the forward end formation to house the rotor in said chamber.

15. The dental appliance of claim 14 wherein the body, hinge and closure are molded of plastic in one piece.

16. The dental appliance of claim 15 wherein said closure mates with said forward end formation on a plane which is perpendicular to the axis of said bore in the extension.

*17. A dental appliance comprising:*

*an elongated hollow body comprising a tubular handle and a tubular extension extending from the handle at one end thereof, the extension having a bore therethrough from the end thereof at the handle to its other end constituting its forward end, the extension having at its forward end a recessed forward end formation defining a forwardly opening recess;*

*a closure for said recess mating with said recessed forward end formation on said recess;*

*said recessed forward end formation of the extension and said closure defining a chamber at said forward end of the extension when said closure is applied to said recessed forward end formation;*

*a rotor rotatable in the chamber on an axis transverse to the axis of the bore;*

*a drive shaft extending through said bore having a forward end in said chamber;*

*a gear on the forward end of the drive shaft mating with a gear on the rotor;*

*said end formation and closure being formed with cooperable bearing recesses which mate in directly opposed relationship to provide generally cylindric bearing means for the rotor when the closure mates with said end formation; and*

*said closure being hinged to said forward end formation for movement between an open position in which the closure is away from said forward end formation of the tubular extension of the body and a closed position in which the closure mates with said forward end formation.*

* * * * *